United States Patent [19]

Jayaraman et al.

[11] Patent Number: 5,132,215

[45] Date of Patent: Jul. 21, 1992

[54] METHOD OF MAKING DOUBLE-STRANDED DNA SEQUENCES

[75] Inventors: Krishna Jayaraman, Fairport, N.Y.; Brent A. Burdick, Columbia, Md.; Fred T. Oakes, Rochester, N.Y.

[73] Assignee: Eastman Kodak Company, Rochester, N.Y.

[21] Appl. No.: 244,871

[22] Filed: Sep. 15, 1988

[51] Int. Cl.$^5$ .............................................. C12P 19/34
[52] U.S. Cl. ...................................... 435/91; 435/172; 435/6; 536/27
[58] Field of Search ................. 536/27, 28, 29; 435/68

[56] References Cited

U.S. PATENT DOCUMENTS 4,458,066 7/1984 Caruthers et al. .
4,503,151 3/1985 Paddock .......................... 435/68
4,683,195 7/1987 Mullis et al. .

OTHER PUBLICATIONS

Maniatis et al., "Molecular Cloning", Cold Spring Harbor Laboratories, 1982, see pp. 242–243, see chapter 4, 7 particularly.
New England British Catalog, 1986/87, see pp. 60–68 particularly.
L. J. McBride et al, Tetrahedron Letters, 24:245–48 (1983).
S. L. Beaucage et al, Tetrahedron Letters, 22:1859–62 (1981).

Primary Examiner—Johnnie R. Brown
Assistant Examiner—L. Eric Crane
Attorney, Agent, or Firm—John R. Everett

[57] ABSTRACT

A method of synthesizing double-stranded DNA sequences is disclosed. The method comprises the steps of:

(a) preparing a first series of oligodeoxyribonucleotide fragments which, when joined in proper sequence, form a DNA coding strand;

(b) preparing a second series of oligodeoxyribonucleotide fragments which, when joined in proper sequence, form a DNA strand complementary to the coding strand;

(c) compelling hydrogen bonding and ligation in proper sequence between the first and second series of oligodeoxyribonucleotide fragments prepared in steps (a) and (b) in a single reaction to produce the entire double-stranded DNA sequence;

(d) treating the double-stranded DNA sequence with one oligonucleotide primer for each strand under hybridizing conditions;

(e) polymerizing an extension product of each primer that is complementary to each strand of the double-stranded DNA sequence which is a template for forming the primer extension product;

(f) denaturing the product of step (e) to separate the primer extension products from their respective templates to form four separate single-stranded DNA sequences;

(g) treating the denatured product of (f) with oligonucleotide primers, such that a primer extension product is synthesizing using each of the single strands produced in step (f) as a template resulting in amplification of the double-stranded DNA sequence; and (h) repeating steps (d), (e), (f) and (g) until the desired quantity of the double-stranded DNA sequence is formed.

7 Claims, 1 Drawing Sheet

METHOD OF MAKING DOUBLE-STRANDED DNA SEQUENCES

FIELD OF THE INVENTION

This invention relates to a method of making double-stranded DNA sequences and to a method of characterizing such sequences.

BACKGROUND OF THE INVENTION

Genetic information is encoded on double-stranded deoxyribonucleic acid (DNA) comprising a coding strand and a complementary strand. The genetic information is encoded on the coding strands according to the order the characteristic repeating nucleotide bases are presented. The DNA coding strand comprises long sequences of nucleotide triplets called "codons" which encode specific bits of information. For example, three nucleotides read as ATG (adenine-thyminie-guanine), result in an mRNA signal interpreted as "start translation". Termination codons TAA and TAG are interpreted as "stop translation". Between the start and stop codons, lie the so-called structural gene having codons that define an amino acid sequence.

Synthetic genes offer a number of advantages over their cloned counterparts since they can be designed for optimal expression and flexibility in subsequent manipulations. In addition, they facilitate the study of structure-functional relationships in proteins through the ability to effect mutations through mutagenesis. However, a synthetic gene is a viable option only if it can be synthesized in a reasonably short time in comparison with procedures to isolate the corresponding complementary DNA.

Various methods for making synthetic genes are known. For example, phosphotriester or phosphodiester methods are sometimes used to prepare oligodeoxyribonucleotide fragments. The fragments are then joined together to form longer strands of repeating nucleic acids. U.S. Pat. No. 4,356,270 describes the synthesis and cloning of the somostatin gene comprising about 56 base pairs.

The phosphodiester method of synthesizing genes is disclosed by Brown, E. L. et al, *Meth. Enzymol.*, 68,109 (1979). This method also involves the synthesis of oligonucleotides (oligos) which are subsequently joined together to form the desired nucleic acid sequence.

Methods exist for making genes in large amounts from small amounts. In general, these methods involve the cloning of the gene in an appropriate host system using the techniques of recombinant DNA. In these techniques, the gene is inserted into an appropriate vector which is used to transform a host organism. When the host organism is cultured, the vector is replicated, and hence more copies of the desired gene are produced. Such techniques are disclosed, for example, in Maniatis, T. et al, *Molecular Cloning: A Laboratory Manual*, Coldspring Harbor Laboratory, pages 390–401 (1982) and aforementioned U.S. Pat. No. 4,356,270.

Current synthetic methods for making genes suffer from several disadvantages. The methods are generally labor-intensive and require a plurality of reaction and isolation steps. It is difficult to make double-stranded DNA sequences greater than 1,000 base pairs in length using such methods because of the numerous side reactions that occur during the chemical synthesis.

The cloning techniques used to produce genes in quantity are also labor-intensive and expensive, requiring multiple steps of editing the gene and the vector into which the gene is inserted, cloning, and separating the cloned gene.

Clearly, the production of double-stranded DNA sequences comprising genetic codes would be enhanced by a method which eliminated the multiple reactions, cloning and isolation steps currently required in the synthetic production of double-stranded DNA.

SUMMARY OF THE INVENTION

Figure 1:
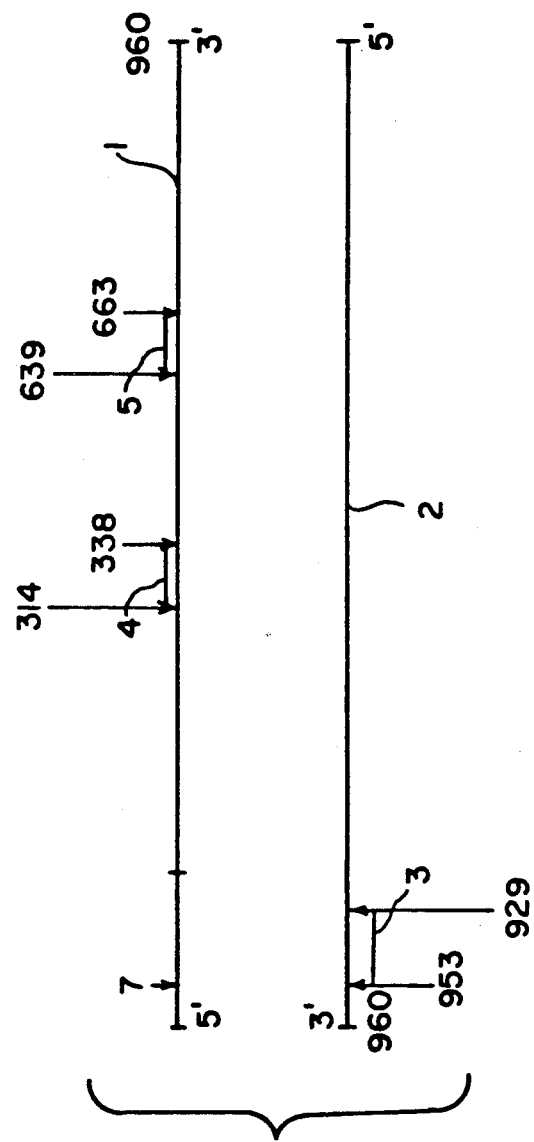
FIG. 1 is a schematic drawing of the horseradish peroxidase gene and associated primers used in example 2 to illustrate the method of DNA characterization provided by this invention.

The above-cited disadvantages of the prior art are substantially ameliorated by the present invention. The present invention provides a method of synthesizing double-stranded DNA sequences, comprising the steps of:

(a) preparing a first series of oligodeoxyribonucleotide (oligo) fragments which, when joined in proper sequence, form a DNA coding strand;

(b) preparing a second series of oligodeoxyribonucleotide (oligo) fragments which, when joined in proper sequence, form a DNA strand complementary to the coding strand;

(c) compelling hydrogen bonding and ligation in proper sequence between the first and second series of oligodeoxyribonucleotide (oligo) fragment prepared in steps (a) and (b) in a single step involving simultaneous joining of all the oligonucleotide fragments to produce the entire double-stranded DNA sequence;

(d) treating the double-stranded DNA sequence with one oligo primer for each strand under hybridizing conditions;

(e) polymerizing an extension product of each primer that is complementary to each strand of the double-stranded DNA sequence which is a template for forming the primer extension product;

(f) denaturing the product of step (e) to separate the primer extension products from their respective templates to form four separate single stranded DNA sequences;

(g) treating the denatured product of (f) with oligo primers, such that a primer extension product is synthesized using each of the single strands produced in step (f) as a template, resulting in amplification of the double-stranded DNA sequence; and (h) repeating steps (d), (e), (f) and (g) until the desired quantity of the double-stranded DNA sequence is formed.

Separation of the resulting double-stranded DNA sequence can be carried out if desired. However, the product of step (h) can be used directly in procedures such as cloning. Also, the desired double-stranded DNA sequence may be isolated from the mixture resulting from step (c) before proceeding with step (d). The isolation may be carried out on a low melting gel. The gel, containing the sequence, may be used directly in step (d).

Using the method provided by this invention, the multiple reactions to a) hydrogen bond various oligo fragments together in a double strand and b) to ligate a plurality of intermediate double-stranded oligo fragments to form a synthetic double-stranded DNA sequence bearing a genetic code are eliminated. In the present invention all of the hydrogen bonding and ligation to form the double-stranded DNA is carried out in a single step. Moreover, this method provides such double-stranded DNA sequences in large amounts without the need to use the cumbersome recombinant DNA technique involving vectors and cloning.

The method also provides a means of characterizing double-stranded DNA sequences, especially when the worker has a knowledge of what the double-stranded sequence should be. This method of characterization comprises the steps of:

(a) providing a double-stranded DNA sequence to be characterized and used as templates;

(b) preparing a first series of oligo primers which, when joined in proper sequence, yield the expected coding strand of the double-stranded DNA sequence;

(c) preparing a second series of oligo primers which, when joined in proper sequence, yield a DNA strand complementary to the coding strand;

(d) arbitrarily selecting a first oligo primer for the coding strand and a second oligo primer for the complementary strand;

(e) treating the double-stranded DNA sequence with the selected oligo primer for each strand under hybridizing conditions;

(f) polymerizing an extension product of each primer that is complementary to at least a portion of each strand of the double-stranded DNA sequence which is a template for forming the primer extension product;

(g) denaturing the product of step (f) to separate the primer extension products from their respective templates to form four separate single stranded DNA sequences;

(h) treating the denatured product of (g) with oligo primers, such that a primer extension product is synthesized using each of the single strands produced in step (g) as a template resulting in amplification of the double-stranded DNA sequence;

(i) repeating steps (e), (f), (g) and (h) until the desired quantity of the primer extension product is formed;

(j) determining whether the primer extension products are of the expected size and composition by comparison to a standard having the expected size and composition; and (k) repeating steps (a)–(j) for each remaining oligo primer prepared in steps (b) and (c).

DETAILS OF THE INVENTION

Essentially, the method of the present invention comprises preparing the synthetic gene followed by amplification thereof. The method is new and unobvious in that 1) the gene is assembled from oligonucleotide fragments in a single step and 2) a polymerase chain reaction is used to amplify the assembled gene.

PREPARATION OF GENE

The oligo fragments and primers used to amplify the properly assembled fragments may be prepared using any suitable method, such as, for example, the phosphite triester, the phosphotriester and phosphodiester methods of the prior art or automated embodiments. In one such automated method diethylphosphoramidites are used as starting materials. They may be synthesized as described by L. J. McBride et al, *Tetrahedron Letters*, 24:25 (1983), U.S. Pat. No. 4,458,066 and Beaucage et al, *Tetrahedron Letters* (1981), 22:1859–1862. A method for synthesizing oligo on a modified solid support is also described in U.S. Pat. No. 4,458,066.

In the present invention all of the fragments of the first and second series are combined together in a single reaction vessel in which the hydrogen bonding and ligation is carried out in a single step. Many other reactions occur during this step in which double-stranded DNA sequences of varying lengths and quantities are also formed.

DNA coding for any polypeptide of known amino acid sequence may be prepared by choosing codons according to the genetic code. For ease in purification, etc., oligo fragments of, for example, from about 50 to about 200 nucleotides are prepared separately, then assembled in one reaction vessel in the desired sequence. Thus, one prepares a first and second series of oligodeoxyribonucleotide (oligo) fragments of convenient size. The first series, when joined in proper sequence, yield a DNA coding strand for polypeptide expression. The second series, when likewise joined in proper sequence, yield a strand complementary to the coding strand. The fragments of the respective strands preferably overlap such that complementarity promotes their self assembly through hydrogen bonding of the cohesive termini of fragment blocks. The structural gene is completed by ligation during the single step.

POLYMERASE CHAIN REACTION (PCR)

The small quantity of the double-stranded DNA sequence, produced in the above described single step involving hydrogen bonding and ligation of the entire set of first and second series of oligo fragments is amplified using a variation of a polymerase chain reaction described in U.S. Pat. No. 4,394,443. The reaction uses primers and polymerization agents.

The PCR technique is conceptually a very simple method for amplifying nucleic acids. It somewhat mimics the natural DNA replication process in that the number of DNA molecules generated by the Polymerase Chain Reaction doubles after each cycle, in a way similar to in vivo DNA replication.

The method is based on the repetition of a set of three steps, all conducted in succession under somewhat different and controlled temperature conditions. The steps are denaturation, annealing and primer extension.

The term "primer" as used herein refers to an oligo sequence that provides an end to which polymerization agents, such as DNA polymerase including *Thermus aquaticus* DNA polymerase, can add nucleotides that are complementary to a nucleotide sequence (template) to which the primer is annealed. The addition occurs in the presence of nucleotides, at a suitable temperature and pH. The primer is single stranded for maximum efficiency in amplification. The primer must be sufficiently long to prime the synthesis of extension products in the presence of the agent for polymerization. The exact lengths of the primers will depend on many factors, including the temperature and source of primer. For example, depending on the complexity of the target sequence, the oligo primer typically contains 15–25 or more nucleotides, although it may contain fewer nucleotides. Short primer molecules generally require cooler temperatures to form sufficiently stable hybrid complexes with template.

The primers are selected to be "substantially" complementary to their templates. This means that the primers are sufficiently complementary to hybridize with their templates. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases of longer sequences can be interspersed into the primer, provided that the primer sequence has sufficient complementarity with the sequence of the strand to be amplified to hybridize therewith and thereby form a template for synthesis of the extension product of the other primer.

The primers are prepared using the same methods used to prepare the oligo fragments from which the genes are prepared.

DENATURATION

After isolation of the desired double-stranded DNA sequence, it is necessary to separate the strands so they can each be used individually as templates. Separation of the strands can occur in a separate step or simultaneously with the synthesis of the primer extension products. This strand separation can be accomplished by any suitable denaturing method including physical, chemical or enzymatic means.

One physical method of separating the strands of the nucleic acid involves heating the nucleic acid until it is completely (>99%) denatured. Typical heat denaturation may involve temperature ranging from about 80° to 105° C. for times ranging from about 1 to 10 minutes. Strand separation may also be induced by an enzyme from the class of enzymes known as helicases. The reaction conditions suitable for separating the strands of nucleic acids with helicases are described by *Cold Spring Harbor Symposia on Quantitative Biology*, Vo. XLIII "DNA: Replication and Recombination" (New York: Cold Spring Harber Laboratory, 1978) B. Kuhn et al, "DNA Helicase", pp. 63-67, and techniques for using RecA are reviewed in C. Radding, Ann. Rev. Genetics, 16:405-37 (1982).

The two strands, once dissociated, will remain free in solution until the temperature is lowered sufficiently to allow annealing.

ANNEALING OF EXTENSION PRIMERS

When the complementary strands of the nucleic acid or acids are separated, the strands are ready to be used as a templates for the synthesis of additional nucleic acid strands.

The extension primers are the pair of synthetic oligos which anneal to sites on the template flanking the region to be amplified. Each primer in the pair will anneal to only one of the strands of DNA. The sequence of the primers is determined by the sequence of the DNA template, at the boundaries of the region to be amplified. Since the primers anneal to opposite strands, they can be viewed as having their 3' ends facing each other. Typically, the primers have different sequences and are not complementary to each other.

Generally the primers are present in large excess over the DNA template. This favors the formation of the primer-template complex over the reassociation of the two DNA strands, at the primers' annealing sites, when the temperature is lowered.

Generally, annealing occurs in a buffered aqueous solution at a pH of 7-9, preferably about 8. Preferably, a molar excess (for cloned nucleic acid, usually about 1000:1 primer:-template, and for genomic nucleic acid, usually about $10^6$:1 primer:template) of the two oligonucleotide primers is added to the buffer containing the separated template strands.

PRIMER EXTENSION (AMPLIFICATION)

The third step in the procedure is the DNA Polymerase-mediated (5'→3') extension of the primer. The conditions under which the extension step is conducted depend directly on the type of DNA Polymerase used. Through this process, the extension primers will become incorporated into the amplification product.

In the PCR technique, the typical set of three steps (i.e., denaturation, annealing, extension) is referred to as a cycle. As taught by U.S. Pat. No. 4,394,443, the technique is carried out on long pieces of DNA. The amplified product of interest is referred to as "short product", which is defined as the region comprised between the 5' ends of the extension primers. Since the primers have well-defined sequences, the short product will have discrete ends, corresponding to the primers' sequences. As the number of cycles increases, the short product will rapidly become the predominant template to which the extension primers will anneal. In theory, the amount of short product will double after each cycle, leading to an exponential accumulation.

In the present invention PCR is used in gene synthesis to amplify the product of interest which is referred to as a long product comprising a desired genetic code. After a few cycles, the long product is preferentially amplified over short products which are intermediates formed during gene synthesis. When several oligo fragments are ligated in a single step, intermediate fragments which are shorter in size than the product are also likely to be formed. By using primers which flank the desired genetic code, the long product, comprising a genetic code, is preferentially amplified over the intermediate side products. Amplifying "short product" in preference to long product has been used in the characterization of synthetic genes (example 2, infra) wherein sections only of the whole gene are amplified.

The actual primer extension and amplification is carried out as follows. The deoxyribonucleotide triphosphates, dATP dCTP, dGTP and dTTP are also added to the synthesis mixture in adequate amounts and the resulting solution is heated to about 90°-100° C. for 1 to 10 minutes, preferably from 1 to 4 minutes. After this heating period the solution is allowed to cool to 20°-55° C., which is preferable for primer hybridization. An agent for polymerization is added to the cooled mixture. The reaction is allowed to occur under conditions known in the art. This synthesis reaction may occur at room temperature up to a temperature above which the agent for polymerization no longer functions efficiently. Thus, for example, if DNA polymerase is used as the agent for polymerization, the temperature is generally no greater than about 45° C.

The agent for polymerization may be any compound or system which will function to accomplish the synthesis of primer extension products including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzyme, which will facilitate combination of the nucleotides in the proper manner to form the primer extension products which are complementary to each nucleic acid strand. At higher temperatures up to 65° to 75° C., the thermostable polymerization agent, *Thermus aquaticus* (Taq), DNA polymerase is used. Generally, the synthesis will be initiated at the 3' end of each primer and proceed in the 5' direction along the template strand, until synthesis terminates.

There may be agents, however, which initiate synthesis at the 5' end and proceed in the other direction, using the same process as described above.

The newly synthesized strand and its template form a double-stranded molecule which is used in the succeeding steps of the process. The succeeding steps of the process again involve repeated application of the set of three steps (denaturation, annealing and primer extension).

New nucleic acid is synthesized on the single-stranded molecules. Additional inducing agent, nucleotides and primers may be added if necessary for the reaction to proceed under the conditions prescribed above. Again, the synthesis will be initiated at one end of the oligo primers and will proceed along the single strands of the template to produce additional nucleic acid. After this step, half of the extension product will consist of the specific nucleic acid sequence bounded by the two primers.

The polymerase chain reaction (PCR) can be performed in a step-wise fashion where after each step new reagents are added. Or it can be performed simultaneously, where all reagents are added at the initial step, or partially step-wise and partially simultaneous, where fresh reagent is added after a given number of steps.

If a method of strand separation, such as heat, is employed which will inactivate the agent for polymerization, as in the case of a heat-stable polymerization agent, then it is necessary to replenish the agent after every strand separation step.

The simultaneous method may be utilized when a number of purified components, including an enzymatic means such as helicase, is used for the strand separation step. In the simultaneous procedure, the reaction mixture may contain, in addition to the nucleic acid strand(s) containing the desired sequence, (1) the strand-separating enzyme (e.g., helicase), (2) an appropriate energy source for the strand-separating enzyme, such as rATP, (3) the four nucleotides, (4) the oligonucleotide primers in molar excess, and (5) the polymerization agent.

If heat is used for denaturation in a simultaneous process, a heat-stable inducing agent such as the thermostable polymerase referred to above may be employed. Each step of the process will occur sequentially notwithstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction.

CHARACTERIZATION OF DNA SEQUENCES

In the polymerase chain reaction, the length of the primer extension product, which predominates after several amplification steps, depends upon the initial position of the primer on its template. This property of the reaction allows one to predict the size and composition of an expected primer extension product based on an expected size and composition of the template extending to the 5' direction to the position of the primer on the template. Using different primers in different positions on the template, the DNA sequence of DNA strands can be characterized with the polymerase chain reaction.

EXAMPLE 1

Synthesis of tuna and horseheart cytochrome c and horseradish peroxidase (HRP) genes.

Production of the Oligo Fragments

The DNA sequences of the genes were derived from the amino acid sequences using yeast preferred codons. The amino acid sequence of each of the genes is described in E. Nargoliash et al, *Nature*, 192, 1125-1127, (1961) (horse cytochrome c); G. Kriel et al, *Z. Physiol Chem.*, 334, 153-166 (1963) (tuna cytochrome c); and K. G. Welidner, *FEBS Letters*, 72, 19-23 (1976) (horseradish peroxidase).

A set of 16 separate oligo fragments of 40-60 bases in length were produced for synthesizing tuna cytochrome c gene. A set of 6 separate oligo fragments of 100-130 bases in length were provided for the synthesis of horseheart cytochrome c gene. A set of 18 separate oligo fragments of 78-135 bases in length were produced for the synthesis of the HRP gene. Each set of fragments had the following characterization. Each set comprises a) a first series to make up the coding strand of the gene and b) a second series to make up a complementary strand.

PREPARATION OF OLIGONUCLEOTIDE FRAGMENTS USING PHOSPHORAMIDITE CHEMISTRY

Each oligo fragment was synthesized on a 0.2 μmole scale on either Applied Biosystem's Model 380-B or Biosearch Model 875D DNA synthesizers which embodies the following method based on phosphoramidite chemistry.

Stepwise the method used was as follows:

1) A support was used which was either a 0.2 μmole or 1 μmole controlled pore glass column (CPG, 500 or 1,000 A° pore size). A nucleoside, A or G or C or T was covalently attached to the support through the 3'-hydroxyl of the nucleoside. The nucleoside contains a 5'-dimethoxytrityl group and a base protecting group (benzoyl or isbutyryl) in the case of nucleosides A, G and C.

2) Removing the 5'-dimethoxytrityl group with 2% Trichloroacetic acid in dichloromethane.

3) Washing the column thoroughly with anhydrous acetonitrile.

4) Adding the next appropriate nucleoside-3'-β-Cyanoethyl phosphoramidite (0.1M, 10 fold molar excess) and tetrazole (0.2M, 20 fold molar excess) and react for 30 seconds at room temperature to form an internucleotide phosphite linkage.

5) Washing the column with acetonitrile to remove excess phosphoramidite.

6) Capping any unreacted 5' hydroxyl groups with an equal mixture of acetic anhydridelutidine-tetrahydrofuran (1:1:8) and dimethylaminopyridine in tetrahydrofuran (6.5% W/V).

7) Washing the column with acetonitrile to remove excess capping reagent.

8) Oxidizing the internucleotide phospite to phosphate using a mixture of 0.1M iodine in a water-pyridine-tetrahydrofuran mixture (1:10:40).

9) Washing the column with acetonitrile to remove excess oxidizing agent.

Steps 2-9 were followed again to add the next nucleotide. Steps 2-9 were repeated until the entire fragment was assembled. At the end of synthesis the 5'-dimethoxytrityl group of the oligo was cleaved and washed with acetonitrile. The column was then treated with concentrated ammonium hydroxide for 2 hours at room temperature to cleave the oligonucleotide from the support. All these steps described so far were automated and carried out on a DNA synthesizer.

Fresh ammonium hydroxide solution is then added to the solution containing the fragment and incubated at 55° C. for 6-16 hours to remove the base protecting groups. The resulting deblocked fragments in solution were then passed through a Sephadex G-25 or G-50 column to remove ammonium hydroxide and benzamides) K. Jayaraman, *Biotechniques* 5, 627 (1987). Approximately 200 μg of the partially purified oligonucleotide was electrophoresed through a 15% polyacrylamide gel containing 7M urea. The product band was visualized by UV shadowing and the band was eluted using standard procedures. The product was desalted on a C-18 Sep Pak column to yield a pure nucleotide fragment. Each fragment was prepared in the same way.

Phosphorylation of the oligonucleotides

Oligos (25 pmoles) were 5'-phosphorylated in a mixture (15 μL) containing 50 mM tris-HCl pH 20, 10 mM MgCl$_2$, 100 mM dithiothrietol (DTT), 500-1000 pmoles of adenosine-5'-triphosphate (ATP) and 1-2 units of T4 polynucleotide kinase. This step enables subsequent ligation. Incubation was for 30-45 minutes at 37° C.

4) Annealing and Ligation of Oligonucleotide Fragments

After phosphorylation, all the oligonucleotides were pooled together, heated up to 90° C. for about 5 minutes, and then slow cooled to room temperature over a period of about 1.5 hours. After cooling, a fresh solution of 10 mm ATP/100 mm DTT was added to a final concentration of 1 mm ATP/10 mm DTT followed by the addition of 40% polyethylene glycol (PEG) of 8000 MW to a final concentration of 5%, 10 units of the DNA ligase was added and incubated either at room temperature for 2 hours or at 12°-16° C. overnight.

5) Analysis of the Ligation Reaction Mixture

The ligated reaction mixture was ethanol precipitated, dried and dissolved in 20 μL water and electrophoresed through a 2% agarose gel. The area corresponding to product, whether or not it could be visualized by UV shadowing, was cut out and electroeluted.

PCR Amplification

The electroeluted material was dissolved in 20 μL water. 0.5 μL of this material was diluted to 200-1000 μL with water and 5 μL aliquots were used as targets for amplification.

Oligo 1 and 16 (from which the tuna cytochrome c gene was assembled) were used as primers for tuna cytochrome C gene.

The primers for horseheart cytochrome c had the DNA sequence:

| | |
|---|---:|
| 1) GAA TT CAT AAT GGG TGA CG TTT GAA | 25 mer |
| 2) GAC CTC TTA TTC GTT AGT AG CCTT | 24 mer |

Primers for HRP gene had the DNA sequence:

| | |
|---|---:|
| GAATT CAT AAT GCA ATT GAC TCCA | Primer 1 |
| GAG CTC TCA TTA GGA GTT GGA GTT | Primer 2 |

Each of the above primers having DNA sequences which are complementary to the 3' end of the coding or complementary strand of the genes with which they are used.

The PCR reactions described herein and U.S. Pat. No. 4,683,195 were carried out using Tag polymerase in 50 μL volume. After 30 and 45 cycles, the reaction mixtures were analyzed on a 4% agarose gel. In each case, the expected product bands were seen.

EXAMPLE 2

Characterization of Synthetic Genes

For prelimary characterization of synthetic genes, PCR can be used. By using different combinations of primers and by checking the product sizes after amplification, one can determine qualitatively whether a gene was constructed as planned. It is very useful to find out if the oligonucleotide and/or the fragments constituting the gene are ligated in the expected order even prior to labor intensive cloning and sequencing. This is illustrated with the HRP gene. The HRP gene obtained from Example 1 was diluted 1:200, and 5 μL aliquots were used for amplification.

In FIG. 1 a schematic drawing of the HRP gene is shown. The gene comprises a coding strand 1 and complementary strand 2. The numbers above the coding strand are numerical positions of nucleotides in the coding strand 1 sequence. Position numbering begins from the 5' end of the gene downstream to the 3' end. Similar position numbering is shown for the complementary strand 2. The position of primers 3, 4 and 5 are also shown.

PCR, for characterization purposes, proceeds according to the following mechanisms using primer 3 for illustration. During the amplification reaction, the primer-extension product will encompass the region between the 5' end of the primer and the end of the complementary strand. The primer-extension product will be the complement of the complementary strand from position 953 (5' of primer) to 1 (end of complementary strand). That primer-extension product will have the same nucleotide sequence as the coding strand from positions 7 to 960. Primer 4 will thus limit subsequent amplifications of the primer extensions to a DNA sequence between positions 7-338 of the coding strand. This same mechanism is true for each primer used. This mechanism is the reason for the predominance of "short products" referred to supra.

| | |
|---|---:|
| 5' GGAT CCG AATT CAT AAT GGG TGA TGT TGC TAAA GGT AAG AAAA CCTTC 3' | Primer 1 |
| 5' GGAT CCG AGCTC TTA CTTAG AAG TGG CTG ATTT CAA GTAG 3' | Primer 16 |

Using primers 3 and 4, PCR was carried out. Primer 4 primes beginning at bases 338, from the 5' end. The expected primer-extension product size is about 330 b.p. (338 to 7). When primers 3 and 5 were used, the expected primer-extension product size is about 660 b.p. (663 to 7). If the oligonucleotides and/fragments were ligated in an incorrect order, expected product sizes from these amplifications would not be obtained. This procedure was repeated with a plurality of primers that in the aggregate covered both the coding and complementary strand of the entire gene. In all cases the expected product sizes were obtained.

While the invention described herein has been demonstrated as successful for three specific genes mentioned in the examples, it will be appreciated that heterologous DNA coding for virtually any known amino acid sequence may be employed, mutatis mutandis to the production of poly(amino)acids, such as polyleucine and polyalanine; enzymes; serum proteins; analgesic polypeptides, such as β-endorphins, which modulate thresholds of pain; mammalian hormones or intermediates therefor, e.g., somatostatin, human insulin, human and bovine growth hormone, leutinizing hormone, ACTH, pancreatic polypeptide, etc; and intermediates include, for example, human preproinsulin, human proinsulin, the A and B chains of human insulin and so on. It will also be understood that double-stranded DNA sequences prepared by the method of this invention can be cloned using conventional recombinant DNA techniques.

The invention has been described in detail with particular reference to preferred embodiments thereof, but it will be understood that variations and modifications can be effected within the spirit and scope of the invention.

We claim:

1. A method of synthesizing double-stranded DNA sequences, comprising the steps of:
    (a) preparing a first series of oligodeoxyribonucleotide fragments which, when joined in proper sequence, form a DNA coding strand;
    (b) preparing a second series of oligodeoxyribonucleotide fragments which, when joined in proper sequence, form a DNA strand complementary to the coding strand;
    (c) compelling hydrogen bonding and ligation in proper sequence between the first and second series of oligodeoxyribonucleotide fragments prepared in steps (a) and (b) in a single reaction to produce the entire double-stranded DNA sequence;
    (d) treating the double-stranded DNA sequence with one oligonucleotide primer for each strand under hybridizing conditions;
    (e) polymerizing an extension product of each primer that is complementary to each strand of the double-stranded DNA sequence which is a template for forming the primer extension product;
    (f) denaturing the product of step (e) to separate the primer extension products from their respective templates to form four separate single-stranded DNA sequences;
    (g) treating the denatured product of (f) with oligonucleotide primers, such that a primer extension product is synthesizing using each of the single strands produced in step (f) as a template resulting in amplification of the double-stranded DNA sequence; and
    (h) repeating steps (d), (e), (f) and (g) until the desired quantity of the double-stranded DNA sequence is formed.

2. The method of claim 1 wherein the double-stranded DNA sequence of step c) is isolated before proceeding to step d).

3. The method of claim 2 wherein the isolation is carried out on a low melting gel and the gel containing the double-stranded DNA sequence is used directly in step d).

4. The method of claim 1 wherein the double-stranded DNA sequence comprises a genetic code.

5. The method of claim 4 wherein the genetic code is in excess of 200 base pairs.

6. The method of claim 4 wherein the genetic code comprises from 2 to 3 kilobases.

7. A method of characterizing double-stranded DNA sequences, comprising the steps of:
    (a) providing a double-stranded DNA sequence to be characterized;
    (b) preparing a first series of oligodeoxyribonucleotide fragments which, when joined in proper sequence, yield the expected coding strand of the double-stranded DNA sequence;
    (c) preparing a second series of oligodeoxyribonucleotide fragments which, when joined in proper sequence, yield a DNA strand complementary to the coding strand;
    (d) arbitrarily selecting a first primer for the expected coding strand and a second primer for the complementary strand;
    (e) treating the double-stranded DNA sequence with one oligonucleotide primer for each strand under hybridizing condition;
    (f) polymerizing an extension product of each primer that is complementary to each strand of the double-stranded DNA sequence which is a template for forming the primer extension product;
    (g) denaturing the product of step (f) to separate the primer extension products from their respective templates to form four separate single stranded DNA sequences;
    (h) treating the denatured product of (g) with oligonucleotide primers, such that a primer extension product is synthesizing using each of the single strands produced in step (g) as a template resulting in amplification of the double-stranded DNA sequence;
    (i) repeating steps (e), (f), (g) and (h) until the desired quantity of the double-stranded DNA sequence is formed;
    (j) determining whether the primer extension products are of the expected size and composition by comparison to a standard have the expected size and composition; and
    (k) repeating steps (a)–(j) for each remaining oligodeoxyribonucleotide fragment prepared in steps (b) and (c).

* * * * *